United States Patent
Pafumi et al.

(10) Patent No.: US 10,940,098 B2
(45) Date of Patent: Mar. 9, 2021

(54) SERIES OF CAPSULES AND METHOD OF MANUFACTURE, COSMETIC COMPOSITION AND COSMETIC TREATMENT

(71) Applicant: CAPSUM

(72) Inventors: Yan Eric Pafumi, Gardanne (FR); Enric Santanach Carreras, Louey (FR)

(73) Assignee: CAPSUM, Marseilles (FR)

( * ) Notice: Subject to any disclaimer, the term of this patent is extended or adjusted under 35 U.S.C. 154(b) by 243 days.

(21) Appl. No.: 16/317,833

(22) PCT Filed: Jul. 10, 2017

(86) PCT No.: PCT/EP2017/067276
§ 371 (c)(1),
(2) Date: Jan. 15, 2019

(87) PCT Pub. No.: WO2018/015197
PCT Pub. Date: Jan. 25, 2018

(65) Prior Publication Data
US 2019/0262241 A1 Aug. 29, 2019

(30) Foreign Application Priority Data

Jul. 20, 2016 (FR) ........................ 1656911

(51) Int. Cl.
| | |
|---|---|
| *A61K 8/02* | (2006.01) |
| *A23P 10/30* | (2016.01) |
| *A61Q 19/00* | (2006.01) |
| *A61K 8/11* | (2006.01) |
| *B01J 13/04* | (2006.01) |
| *A61K 8/73* | (2006.01) |

(52) U.S. Cl.
CPC ............ *A61K 8/0237* (2013.01); *A23P 10/30* (2016.08); *A61K 8/11* (2013.01); *A61K 8/733* (2013.01); *A61Q 19/00* (2013.01); *B01J 13/046* (2013.01); *A61K 2800/56* (2013.01); *A61K 2800/63* (2013.01)

(58) Field of Classification Search
CPC ........ A61K 8/0237; A61K 8/11; A61K 8/733; A61K 2800/56; A61K 2800/63; A23P 10/30; A61Q 19/00; B01J 13/046
See application file for complete search history.

(56) References Cited

FOREIGN PATENT DOCUMENTS

| | | |
|---|---|---|
| FR | 3024658 A1 | 2/2016 |
| WO | WO 2010/063937 A1 | 6/2010 |
| WO | WO 2011/086331 A2 | 7/2011 |
| WO | WO 2012/089820 A1 | 7/2012 |
| WO | WO 2013/132082 A1 | 9/2013 |
| WO | WO 2013/132083 A1 | 9/2013 |
| WO | WO 2015/071433 A1 | 5/2015 |
| WO | WO 2015/075074 A1 | 5/2015 |

OTHER PUBLICATIONS

International Search Report dated Aug. 21, 2017 in International Application No. PCT/EP2017/067276.
Written Opinion in International Application No. PCT/EP2017/067276, dated Jul. 20, 2016.

*Primary Examiner* — Alma Pipic
(74) *Attorney, Agent, or Firm* — Pearne & Gordon LLP

(57) ABSTRACT

A method of manufacturing a series of capsules (1A) comprising a core (3), and a gelled envelope (5) completely encapsulating the core and comprising at least two external phases (5A, 5B), wherein the gelled envelope has a external surface comprising at least two distinct portions (7A, 7B) formed respectively by the two external phases, and comprising the following steps:

conveying a first flow (F1) that is intended to form the core, and a second flow (F2) of at least the two external phases that are intended to form the gelled envelope, wherein each external phase contains a liquid polyelectrolyte that is able to gel, at least one of the two external phases comprising a coloring agent, while the second flow surrounds the first flux about an axis (D2);

successive formation of a plurality of liquid bodies (57) comprising a drop (107), and a film coating (109) coating the drop and having the two external phases, wherein the film has on its external surface at least two portions (109A, 109B) formed by the two external phases; and immersing each liquid body in a gelling solution (100) adapted to react with the polyelectrolyte of each of the two external phases, and recovering of the plurality of capsules.

Series of capsules, cosmetic composition containing the capsules and cosmetic treatment using the composition.

20 Claims, 6 Drawing Sheets

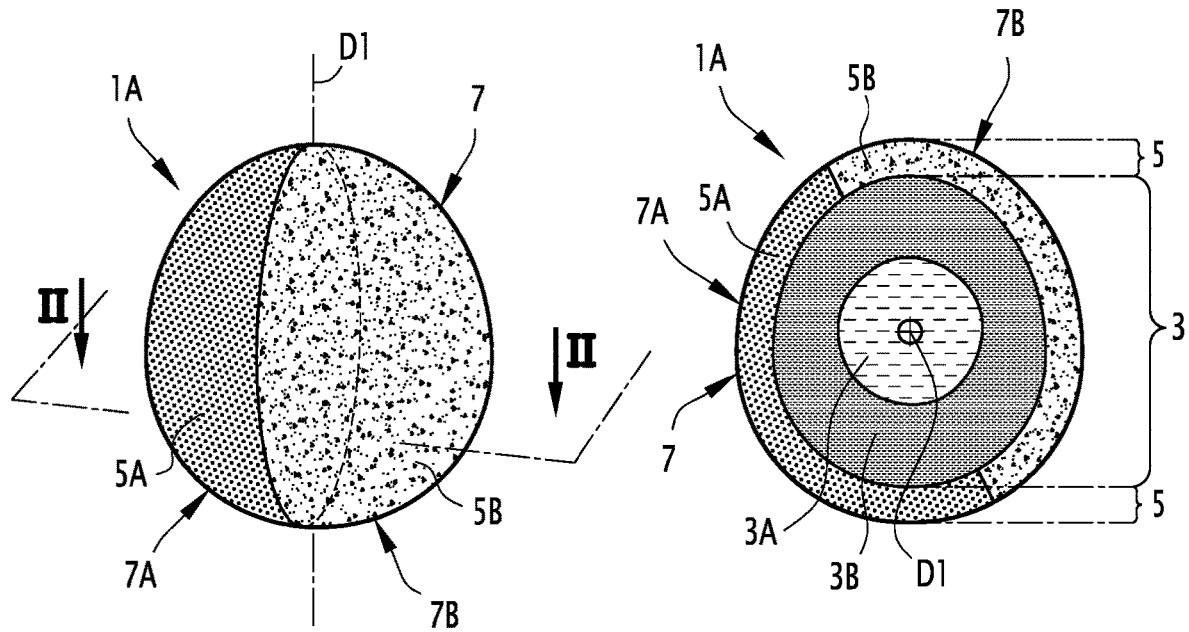
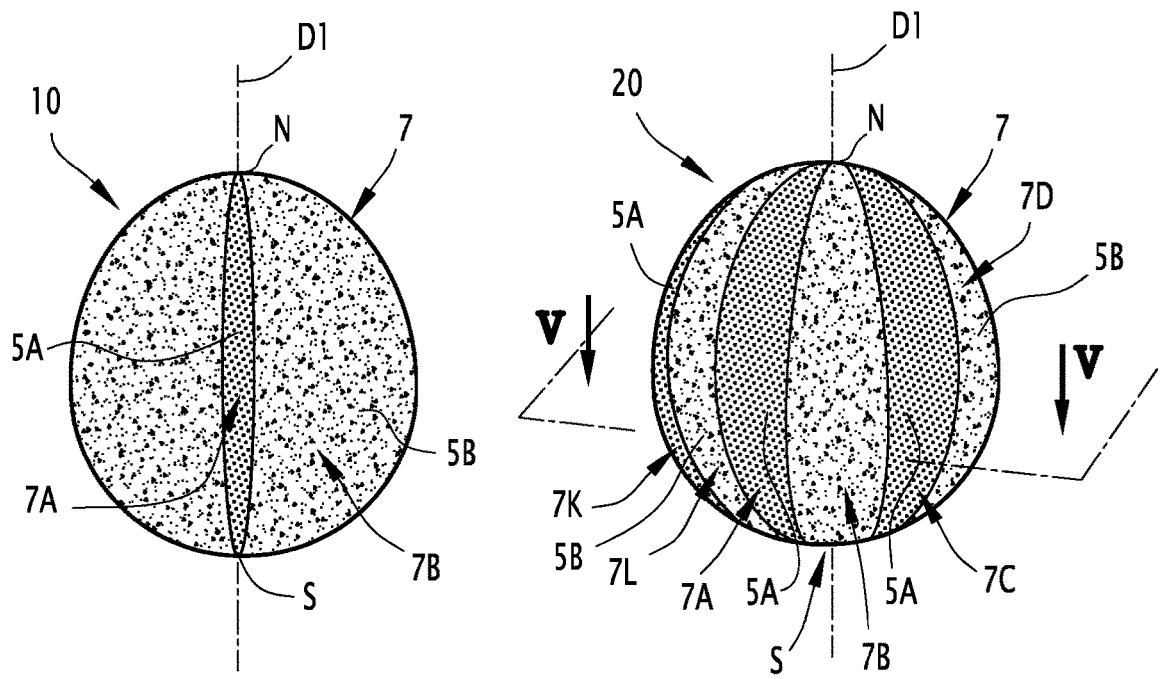

SERIES OF CAPSULES AND METHOD OF MANUFACTURE, COSMETIC COMPOSITION AND COSMETIC TREATMENT

BACKGROUND OF THE INVENTION

Field of the Invention

The present invention relates to the field of compositions, in particular cosmetics compositions, and more specifically to the field of associated manufacturing methods as well as to the methods of application of the compositions to a keratinous material.

The present invention relates more particularly to a method of manufacturing a series of capsules, wherein each capsule comprises a liquid core or at least a gelled portion or at least a thixotropic portion, and a gelled envelope completely encapsulating the core.

The invention also relates to a series of capsules capable of being manufactured by such a method, and a composition, in particular a cosmetic composition, comprising such a series of capsules and a medium for receiving these capsules.

Finally, the invention relates to a non-therapeutic method for the cosmetic treatment of a keratinous material, in particular the skin, comprising at least one step of applying at least this composition to the keratinous material.

Description of Related Art

The Applicant already manufactures and markets cosmetic compositions in the form of an emulsion based on the use of capsules, or beads, that are obtained by millifluidic methods.

According to a first technology, the capsules have an outer layer of calcium alginate and a liquid or gel core. Such a method is advantageous in that the capsules with a diameter of between 1 and 3 mm, have an apparent monodispersity and an envelope having a small thickness. This technology, including a related manufacturing method, is described in WO 2010/063937, WO 2011/086331 and WO 2015/071433.

The method however has some limitations, particularly in terms of texture and the nature of the liquid to be encapsulated. It only allows encapsulation of one type of active ingredient at a time, namely aqueous or oily.

Thus, the Applicant has developed a second and a third technology, which overcome the aforementioned drawbacks.

In the second technology, the capsules comprise a core formed by a drop of oil suspended in an aqueous phase of water, and a fine alginate membrane surrounding the core. The capsule comprises three phases: an internal oily phase, an intermediate aqueous phase and an external phase.

In the third technology, the core is in the form of an aqueous drop suspended in an oily phase. The capsule then comprises three phases: an internal aqueous phase, an intermediate oily phase and an external phase.

In both cases, the intermediate phase has a high viscosity, and is advantageously gelled in order to ensure good suspension of the internal drop in the intermediate phase and to avoid contact between the internal phase with the external phase.

These second and third technologies use the principle of three-path coextrusion.

Three fluids arrive at a nozzle through three different paths and form a three-phase drop. This drop then falls into a calcium bath to which is added a surfactant, particularly a nonionic surfactant, allowing better penetration of the capsule in the calcium bath. The drop in the bath causes gelation of the capsule by diffusion of calcium into the external phase which becomes the gelled membrane. The second and third technologies mentioned above, including the associated manufacturing methods, are described in particular in documents WO 2012/089820 and WO2013/132083.

The use of particles, in particular the capsules described above, in compositions, particularly cosmetic compositions, is known and gives the latter a differentiating and particularly attractive visual appearance, while protecting the encapsulated active ingredients.

The differentiating and attractive nature is sometimes further reinforced by the use, in the membrane and/or the liquid core of the capsules, of coloring agents such as pigments, pearlescent agents, dyes, optical effect materials, in particular liquid crystals, and mixtures thereof.

Nevertheless, the development and provision to consumers of compositions with a novel visual aspect remains a constant objective.

One object of the invention is therefore to provide particles with a new structure giving them an unprecedented visual appearance and a method for manufacturing these particles, wherein the manufacturing must be at a competitive cost.

BRIEF SUMMARY OF THE INVENTION

For this purpose, one object of the invention is a method for manufacturing a series of capsules, wherein each capsule comprises a core which is liquid or at least a partially gelled or at least partially thixotropic core, and a gelled envelope completely encapsulating the core and comprising at least two external phases, wherein each external phase contains at least one gelled polyelectrolyte, wherein the gelled envelope has an external surface that comprises at least two distinct portions formed respectively by the two external phases, wherein the method comprises the following steps:

conveying a first flow of one or more internal phases that is/are intended to form the core, and a second flow of at least the two external phases that are intended to form the gelled envelope, wherein each external phase contains at least one liquid polyelectrolyte that is capable of being gelled, and that is identical or different to at least one of the two external phases comprising at least one coloring agent, wherein the second flow surrounds the first flow about an axis;

successive formation, from the first flow and the second flow, of a plurality of liquid bodies, wherein each liquid body comprises a drop of the internal phase(s), and wherein a peripheral film coats the drop and comprises the two external phases, wherein the film has at least two distinct portions respectively formed by the two external phases on its outer surface; and immersing each liquid body in a gelling solution containing at least one reagent that is designed to react with the polyelectrolyte of each of the two external phases to form one of the capsules, and recovery of the plurality of capsules.

According to particular embodiments, the method comprises one or more of the following features, taken in any technically feasible combination:

it furthermore comprises the application of at least one gaseous flow to each of the liquid bodies being formed in order to deform the two portions of the outer surface of the film by rotation about the axis, wherein the gaseous flow has a tangential component relative to the axis;

during the step of forming the liquid bodies, the two external phases are in contact with the first flow;

the conveying is carried out through at least one nozzle defining the axis, wherein each of the two external phases is in contact with an external envelope of the nozzle leaving the nozzle, and the liquid bodies are formed at an outlet of the nozzle, wherein the method comprises a step of detaching the liquid bodies from the nozzle;

the conveying step comprises an outlet of the second flow of at least one collector formed by the nozzle, wherein the collector surrounds the first flow around a local direction of circulation of the first flow; and supplies the collector from at least two sources supplying the two external phases in order to create a plurality of distinct supply areas in the collector, wherein each of the supply areas is filled by either one of the two external phases, wherein the supply areas are filled by one alternating with those filled by the other around the local direction of circulation;

the nozzle forms a plurality of collector supply channels, wherein each supply channel is connected to one of the two sources and forms an inlet opening in the collector, wherein the inlet openings are angularly successive about the local direction of circulation;

one of the supply areas is supplied with a first flow in one or the other of the two external phases, while another of the supply areas is supplied with a second flow in one or the other of the two external phases, wherein the first flow is lower than the second flow;

the ratio of the first flow rate divided by the total flow rate of the second flow is less than ⅓, preferably less than ¼, or even less than ⅙, in particular less than ⅛, and better still less than 1/10; and the conveying step comprises a physical separation of the first flow and the second flow at the outlet of the nozzle by an envelope of the nozzle.

The object of the invention is also a series of capsules capable of being manufactured by a method as described above, wherein each capsule comprises:

a liquid, or at least partially gelled, or at least partially thixotropic, core, wherein the core comprises one or more internal phases, and a gelled envelope completely encapsulating the core and comprising at least two external phases, wherein each external phase contains a gelled polyelectrolyte, wherein at least one of the two external phases comprises a coloring agent, and wherein the gelled envelope has an external surface comprising at least two distinct portions formed respectively by the two external phases.

According to particular embodiments, the series of capsules comprises one or more of the following characteristics, taken in any technically feasible combination:

for each capsule, the external surface of the gelled envelope comprises a plurality of portions formed by one or the other of the two external phases, wherein the portions form sectors alternating about a polar direction of the capsule;

the sectors extend substantially between one pole of the capsule and an opposite pole in the polar direction, wherein the sectors are substantially delimited either by meridians of the capsule or by curved lines substantially extending between one pole and the opposite pole; and the two external phases of the gelled envelope are in contact with the core.

The object of the invention is also a composition, in particular a cosmetic composition, comprising a series of capsules as defined above, and a medium for receiving these capsules.

Another object of the invention is a non-therapeutic method for the cosmetic treatment of a keratinous material, in particular the skin, comprising at least one step of applying to the keratinous material at least one composition as defined above.

BRIEF DESCRIPTION OF THE SEVERAL VIEWS OF THE DRAWING(S)

The invention will be better understood upon reading the description which follows, given solely by way of example and with reference to the appended drawings, wherein:

FIG. 1 shows a schematic perspective view of a capsule of a series according to a first embodiment of the invention, FIG. 2 shows a schematic view in section essentially in a substantially equatorial plane of the capsule shown in FIG. 1;

FIG. 3 shows a schematic perspective view of a capsule of a series according to a second embodiment of the invention, FIG. 4 shows a schematic perspective view of a capsule of a series according to a third embodiment of the invention.

Figure 5:
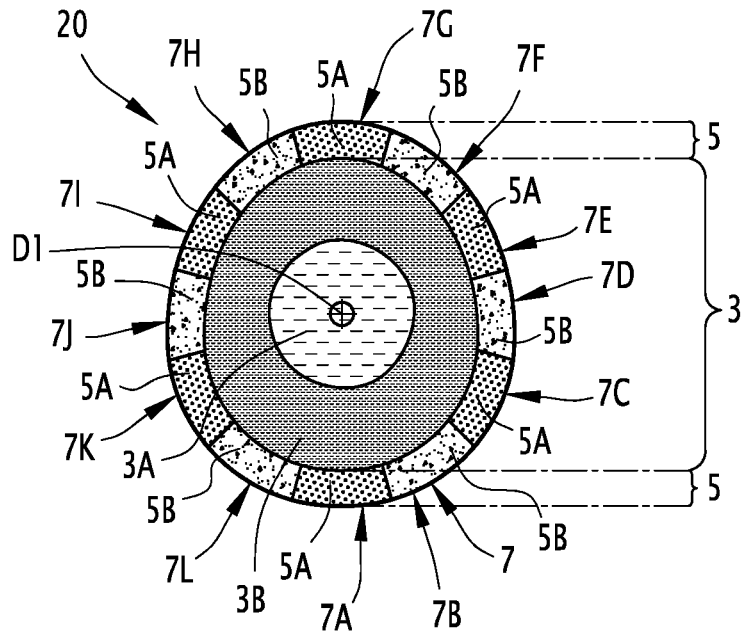
FIG. 5 shows a schematic view in section substantially in an equatorial plane of the capsule shown in FIG. 4.
Figure 6:
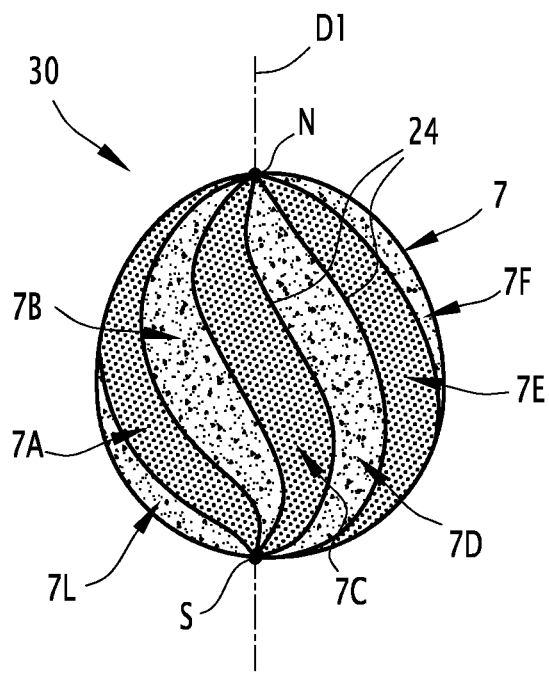
Figure 7:
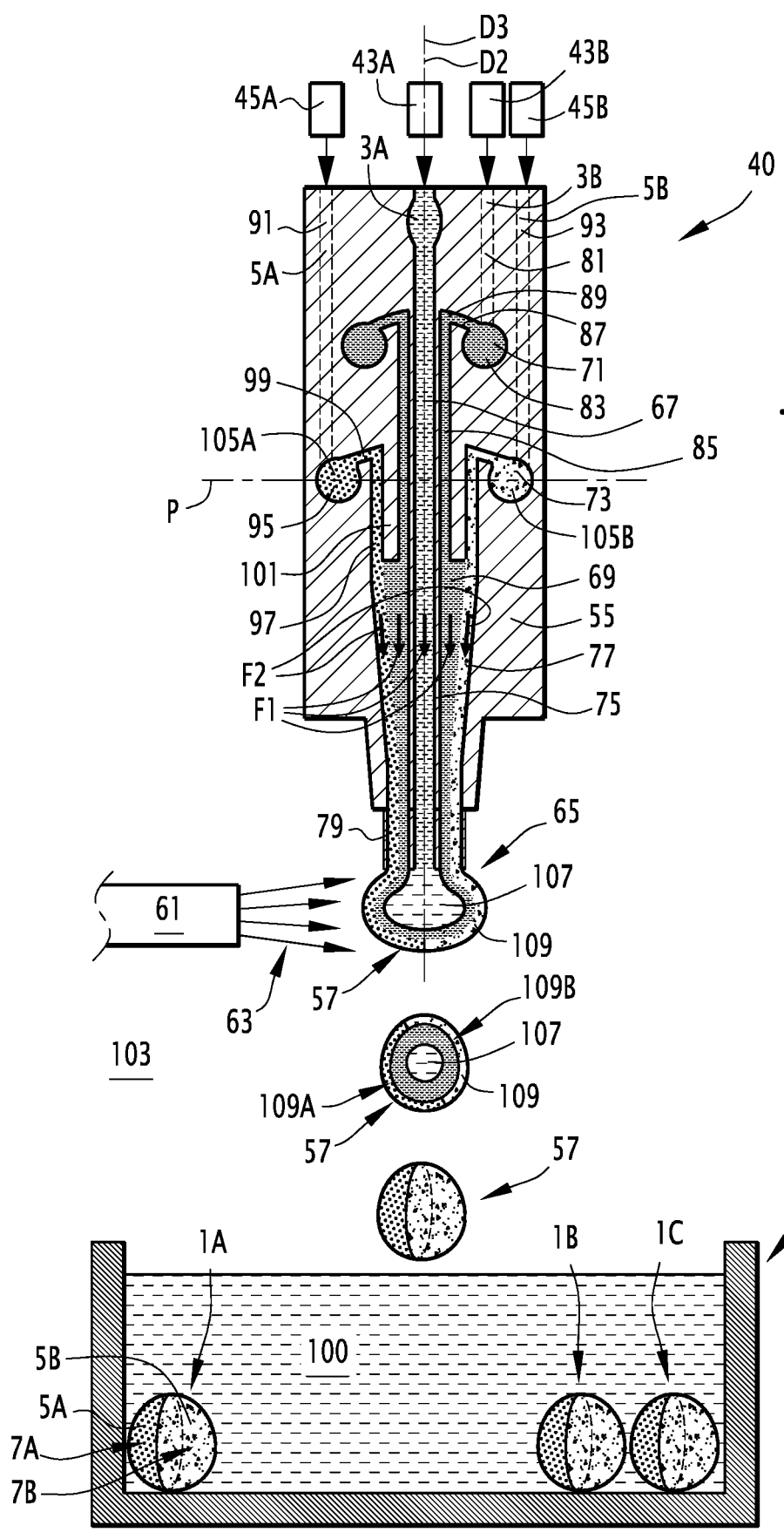
Figure 8:
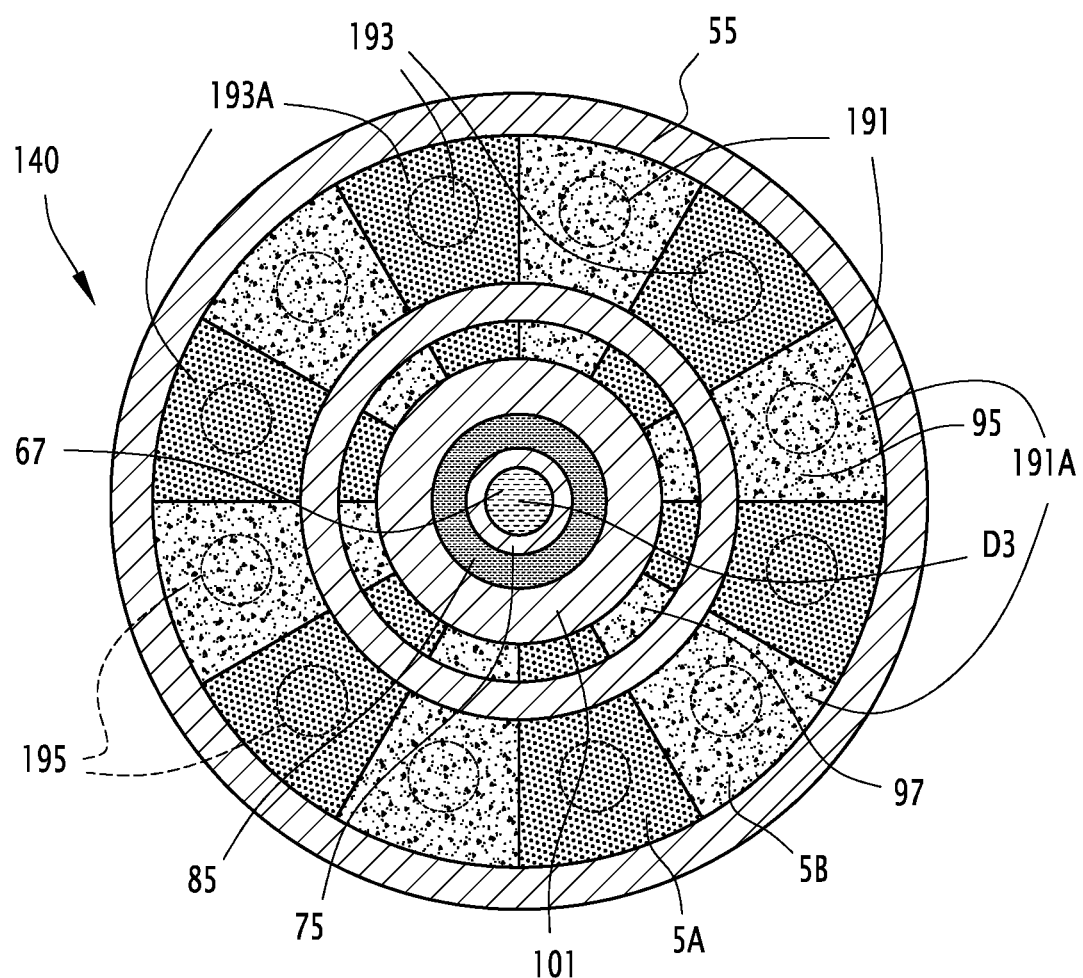
Figure 9:
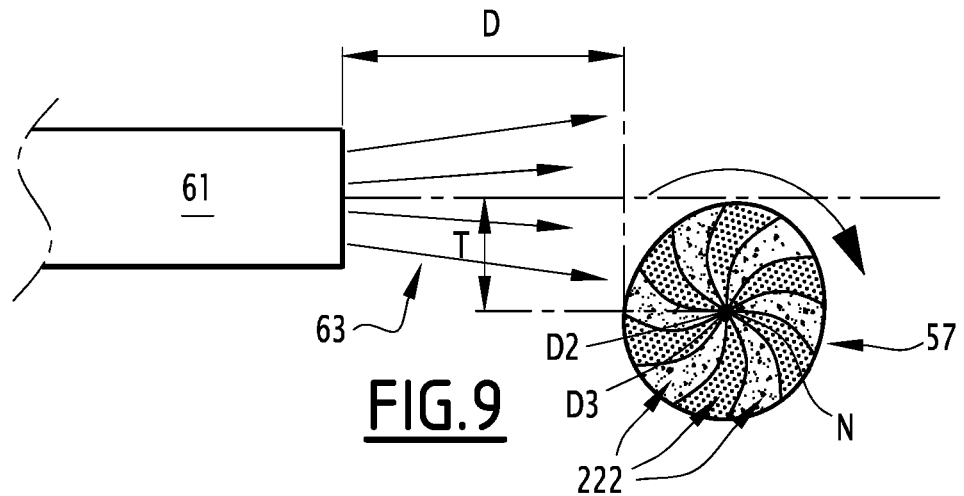
Figure 10:
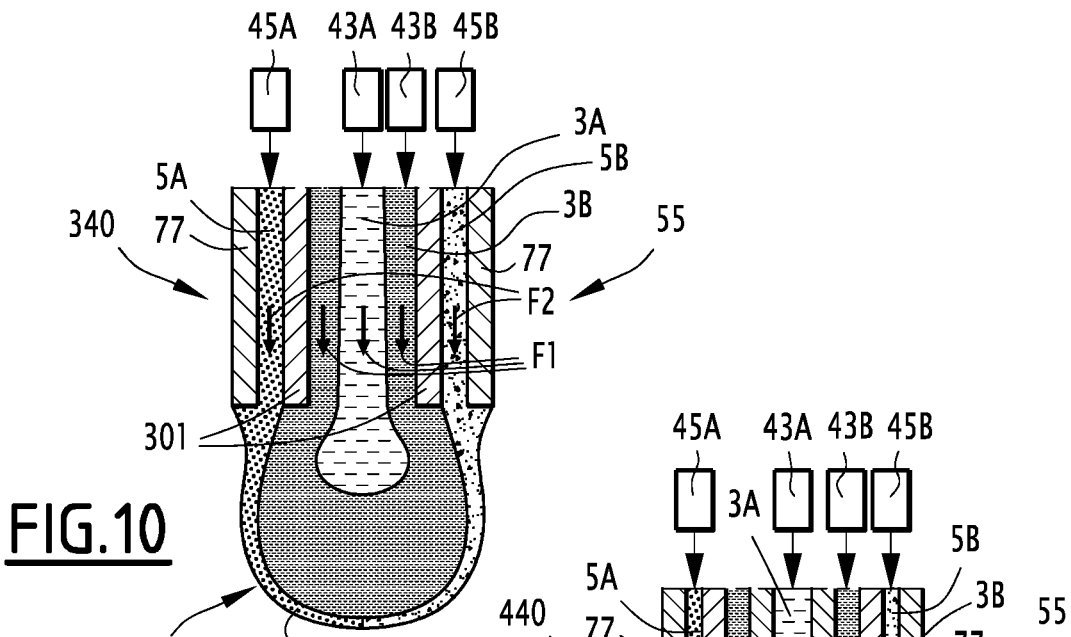
Figure 11:
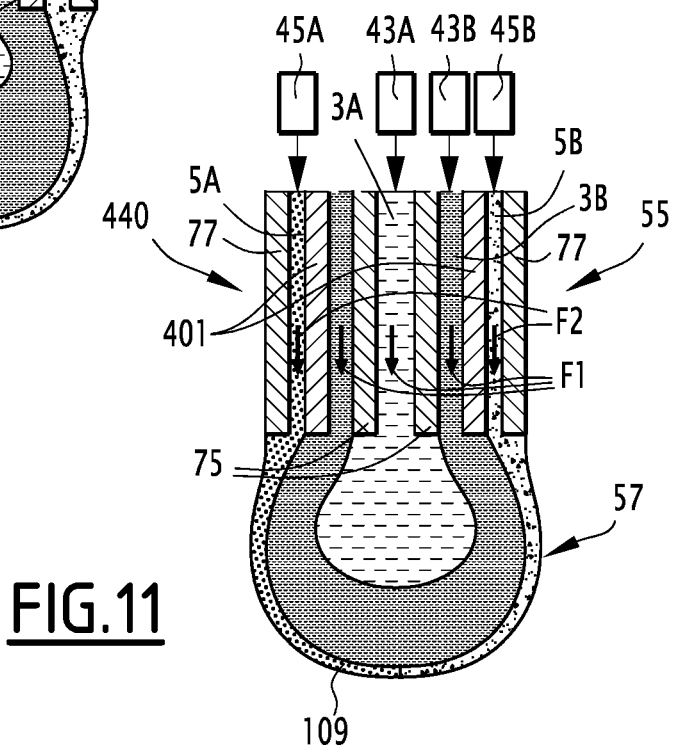
Figure 12:
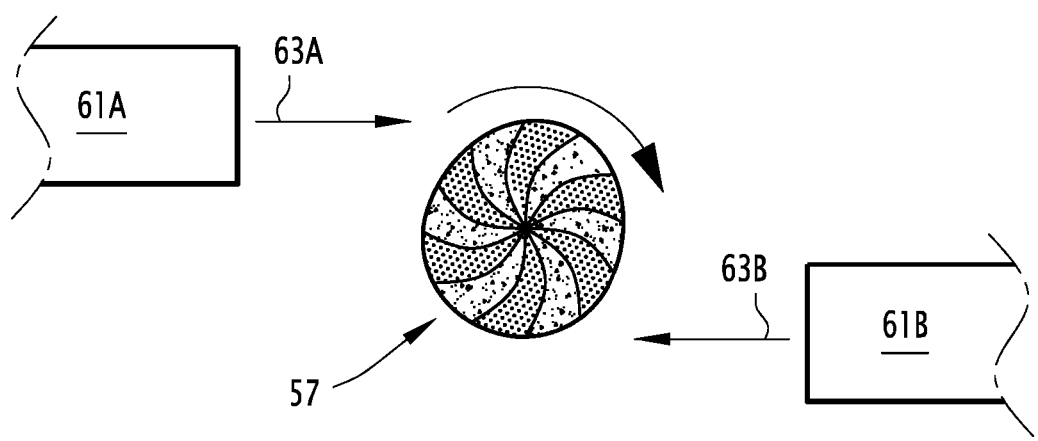

FIG. 6 shows a schematic perspective view of a capsule of a series according to a variant of the third embodiment, FIG. 7 shows a schematic view of a device implementing a manufacturing method according to the invention making it possible to manufacture the capsule represented in FIGS. 1 and 2, FIG. 8 shows a schematic view of a variant of the device shown in FIG. 7, making it possible to manufacture the capsule shown in FIGS. 4 and 5;

FIG. 9 shows a schematic view of the device shown in FIG. 8 that is used to manufacture the capsule shown in FIG. 6, FIGS. 10 and 11 show schematic views of other variants of the device shown in FIG. 7, and FIG. 12 shows a schematic view of a variant of the device represented in FIG. 9.

DETAILED DESCRIPTION OF THE INVENTION

First Embodiment of the Capsules

Referring to FIGS. 1, 2 and 7, a series of capsules 1A, 1B, 1C according to a first embodiment of the invention is described.

As the capsules 1A, 1B, 1C are similar to each other, only the capsule 1A shown in FIGS. 1 and 2 will be described below.

According to a particular embodiment (not shown), the capsules of a series are not analogous to each other. Such a series may be obtained, for example, by mixing capsules of one or more series as described herein.

Preferably, the capsule 1A has a substantially spherical shape and an outside diameter greater than 0.5 mm, advantageously less than 10 mm, and preferably between 1 mm and 5 mm.

The capsule 1A comprises a core 3 that is liquid or at least partially gelled or at least partially thixotropic, and a gelled envelope 5 that completely encapsulates the core.

Advantageously, the volume ratio $R_v$ of the volume of the core 3 to the volume of the gelled envelope 5 is greater than 2, and may be, in particular, greater than 5. This ratio $R_v$ is advantageously less than 50. It may be, for example, between 5 and 10.

In this example, the core 3 has two internal phases 3A, 3B.

The internal phase 3B completely surrounds the internal phase 3A, and constitutes an intermediate phase between the internal phase 3A and the gelled envelope 5.

The gelled envelope 5 defines an external surface 7, wherein the two external phases 5A, 5B form two portions 7A, 7B that are distinct from the external surface.

Each external phase 5A, 5B comprises at least one gelled polyelectrolyte, or may even contain gelled polyelectrolytes that may be identical or different from each other.

At least one of the two external phases 5A, 5B, for example the external phase 5A, further comprises at least one coloring agent.

More generally, the external phases 5A, 5B differ from each other in the presence or absence and/or the nature and/or the content of the coloring agent(s).

The external phases 5A, 5B are, for example, in contact with the core 3.

According to one variant (not shown), some of the external phases, for example the external phase 5B, are not in contact with the core 3.

The coloring agent makes it possible to visually distinguish the portion 7A from the portion 7B and thus to confer a novel visual appearance on the capsules according to the invention.

The coloring agent may be chosen, for example, from pigments, pearlescent agents (glitter), optical effect materials, in particular liquid crystals, and mixtures thereof, preferably pigments and/or nacres. For example, the portion 7A may be colored by the coloring agent, while the portion 7B is not.

According to one variant (not shown), the two portions 7A, 7B are both colored, but are of different colors, by means of a coloring agent or a mixture of coloring agents.

In this example, the portions 7A, 7B have substantially equal areas (for example at +/−5%). The portions 7A, 7B are, for example, substantially hemispherical.

Core

The core 3 of the capsule 1A comprises one or more active ingredients, in one mixture or in separate phases, or in several mixtures in separate phases.

In the context of the present description, the term "active ingredient" means a compound having a beneficial physiological effect on the element on which it acts. It aims, for example, to protect, maintain in good condition, cure, heal, perfume or flavor.

The active ingredient may advantageously be a cosmetic, dermo-pharmaceutical, pharmaceutical, perfume or food ingredient.

The core 3 may contain the active ingredient in the form of a pure liquid, or a solution of the active ingredient in a liquid solvent, or a dispersion such as an emulsion or suspension of the active ingredient in a liquid.

When the active ingredient is a cosmetic agent, it may be chosen from sodium hyaluronate or other moisturizing/repairing molecules, vitamins, enzymes, anti-wrinkle, anti-aging, protective/antiradical agents, antioxidants, soothing, softening, anti-irritant, tensor/smoothing, emollient, slimming, anti-cellulite, firming, shaping, draining, anti-inflammatory, depigmenting, whitening, self-tanning, exfoliating, stimulating cell renewal or stimulating cutaneous microcirculation, absorbing or filtering UV, anti-dandruff, and mixtures thereof.

A cosmetic agent that may be contained in the core 3 is, for example, cited in the Council Directive 93/35/EEC dated 14 Jun. 1993. This product may be, for example, a cream, an emulsion, a lotion, a gel or an oil for the skin (hands, face, feet, etc.), a foundation (liquid, paste) a preparation for baths and showers (salts, mousses, oils, gels, etc.), a hair care product (hair dyes and bleaches), a cleaning product (lotions, powders, shampoos), a hair care product (lotions, creams, oils), a styling product (lotions, lacquers, glossines), a shaving product (soaps, mousses, lotions, etc.), a product intended to be applied to the lips, a sun product, a sunless tanning product, a product for whitening the skin, an anti-wrinkle product.

More particularly, the dermopharmaceutical agents denote the agents acting on the skin.

When the active ingredient is a pharmaceutical agent, it may be advantageously chosen from anticoagulants, anti-thrombogenic agents, anti-mitotic agents, anti-proliferation, anti-adhesion, anti-migration agents, cell adhesion promoters, growth factors, antiparasitic molecules, anti-inflammatories, angiogenics, angiogenesis inhibitors, vitamins, hormones, proteins, antifungals, antimicrobial molecules, antiseptics, antibiotics and their mixtures.

When the active ingredient is a perfuming agent, it may be in the form of a mixture. Among perfuming agents, mention may be made of any type of perfume or fragrance, wherein these terms are used exchangeably here. These perfumes or fragrances are well known to those skilled in the art and include, in particular, those mentioned, for example, in S. Arctander, Perfume and Flavor Chemicals (Montclair, N.J., 1969), S. Arctander, *Perfume and Flavor Materials of Natural Origin*. (Elizabeth, N.J., 1960) and in "*Flavor and Fragrance Materials,*" 1991 (Allured Publishing Co. Wheaton, Ill. USA). The perfumes used in the context of the present invention may comprise natural products such as extracts, essential oils, absolutes, resinoids, resins, concretes, etc. as well as basic synthetic substances such as hydrocarbons, alcohols aldehydes, ketones, ethers, acids, esters, acetals, ketals, nitriles, etc., including saturated and unsaturated compounds, aliphatic, alicyclic and heterocyclic compounds.

The food agents are advantageously purees of vegetables or fruits such as mango puree, pear puree, coconut puree, cream of onions, leeks, carrots, or other preparations that may mix several fruits or vegetables. Alternatively, these may be oils such as a cooking oil, such as olive oil, soybean oil, grape seed oil, sunflower oil, or any other oil extracted from plants, as well as active ingredients such as probiotics, yeasts, vitamins, minerals or oleoactives.

The core 3 may also comprise a coloring agent.

According to one embodiment, the core 3 may be liquid.

According to one particular embodiment, the core 3 may be at least partly gelled. In this case, the core may be, for example, formed by the gelation of a gelling product obtained by a temperature change, in particular by a temperature decrease of at least 10° C. Alternatively, the gelation may be obtained in the presence of ions, other molecules or certain conditions of pH or ionic strength.

The core 3 may contain, for example, a polyelectrolyte gel that is identical to the polyelectrolyte gel of the gelled envelope 5. According to one variant, the core 3 may contain an aqueous solution of a gelling agent that is different from the polyelectrolyte of the gelled envelope 5. The gelling agent may be preferably selected from the group consisting of polysaccharides, galactomannans, polysaccharides, glycosaminoglycans, polyols and mixtures thereof. Advantageously, it may be chosen from the group consisting of xanthan gum, carrageenan, carob, guar gum, gellan, hyaluronic acid, glycerol, propanediol, cellulose or its derivatives, and their mixtures.

When a gelling agent is present in the core 3, it is typically present in a concentration of from 0.01% to 1% by weight relative to the total weight of the core.

According to another particular embodiment, the core 3 may be at least partially thixotropic. By thixotropic phase in the sense of the invention, is meant a phase that is in the liquid state and destructured when flowing, but which is substantially solid or gelled when at rest.

By "liquid when it flows" is meant that the behavior of the phase in question is viscous, i.e. the deformation of the material depends not only on the stress applied but also on the duration of the application of the stress. One way to characterize this behavior is by a creep test using a rheometer on the sample, wherein a characteristic stress of the flows involved during the manufacturing is applied and the deformation curve traced as a function of time (data obtained with the rheometer software). If the curve has a non-zero slope over long periods (more than 30 seconds), the phase may be considered to be liquid. If this slope is zero, the phase may be considered to be solid.

By "solid or gelled at rest" is meant that the deformation of the material only depends on the applied stress. One way of characterizing this behavior is by a creep test on the sample using a rheometer, wherein a stress is applied that is characteristic of stresses undergone by the capsule at rest as a function of time (data obtained with the software of the rheometer). If the curve has a zero slope over long periods (more than 30 seconds), the phase may be considered to be solid. If this slope is non-zero, the phase may be considered to be liquid.

As a thixotropic agent, may be mentioned, for example, colloidal particles (silica, clays, latex, etc.).

When a thixotropic agent is present in the core 3, it is typically present in a concentration of 0.5% to 5% by weight relative to the total weight of the core, or even to the weight of the phase comprising it.

The capsule 1A is called "complex" because the core 3 has at least two internal phases. A complex capsule is, for example, a capsule as described in applications WO 2012/089820 and WO 2013/132083 in the name of the Applicant.

According to one variant (not shown), the core 3 comprises a continuous internal phase 3B, in which there is a plurality of drops of the internal phase 3A.

The active ingredient of the core 3, when present, may be contained in the internal phase 3A and/or in the internal phase 3B.

For example, the inner phase 3B may be aqueous and the inner phase 3A is oily and immiscible with the inner phase 3B at room temperature and atmospheric pressure. This may be referred to as an "oil-in-water" core.

Alternatively, the internal phase 3B may be oily and the internal phase 3A is aqueous and immiscible with the internal phase 3B at room temperature and atmospheric pressure. This may be referred to as a "water-in-oil" core.

The term "aqueous phase" is understood to mean a phase having the property of solubilizing polar and hydrophilic compounds. An aqueous phase preferably comprises water and at least one active ingredient as described above, which is otherwise hydrophilic.

The term "oily phase" is understood to mean a phase having the property of solubilizing apolar compounds, such as fatty substances, oils, lipids. An oily phase preferably comprises a fatty substance, an oil or a mixture of oils of vegetable, animal or mineral origin.

As a vegetable oil may be mentioned, for example, apricot oil, sweet almond oil, jojoba oil, palm oil, argan oil or phytosqualane.

Examples of fatty substances that may be mentioned include esters of fatty alcohols and/or fatty acids, such as isopropyl myristate, glycerol myristate, isononyl isononanoate and acid triglycerides, caprylic or capric acid, isopropyl palmitate and ethyl palmitate.

As an animal oil may be mentioned, for example, squalene.

As mineral oil may be mentioned, for example, hydrogenated polyisobutylene, isododecane, paraffin oils or silicone oils.

The internal phase 3B is advantageously liquid.

In one variant, the internal phase 3A is liquid and the internal phase 3B is thixotropic.

Alternatively, the internal phase 3A may be liquid, while the internal phase 3B may be gelled.

The thixotropy or gelation of the internal phase 3B is advantageous in that it makes it possible to ensure the suspension of the drop of internal phase 3A in the intermediate phase formed by the internal phase 3B in a complex capsule according to the invention. In fact, it helps preserve the integrity of the capsule over time.

The internal phase 3B may further comprise one or more cosmetic, dermo-pharmaceutical, pharmaceutical, perfume or food active ingredients, as defined above.

The internal phase 3B may also comprise excipients that are different from the gelling agents and thixotropic agents previously described, such as thickeners, or rheology modifiers. These thickeners may be, for example, polymers, cross-polymers, microgels, gums or proteins, including polysaccharides, celluloses, polysaccharides, silicone polymers and co-polymers, colloidal particles (silica, clays, latex . . . ).

The internal phase 3B may comprise solid particles, and, in particular, nacre particles.

Advantageously, the internal phase 3B is totally interposed between the internal phase 3A and the gelled envelope 5. The internal phase 3B keeps the internal phase 3A away completely from the gelled envelope 5.

The internal phase 3A may comprise one or more cosmetic, dermo-pharmaceutical, pharmaceutical, perfume or food active ingredients, as defined above.

The internal phase 3A advantageously has a spherical shape.

Alternatively, the internal phase 3A has an elliptical or lenticular shape.

According to another variant, the capsule 1A is a capsule referred to as "solid", i.e. the core also comprises a polyelectrolyte in the gelled state chelated by divalent cations, wherein the polyelectrolyte is identical to that present in the envelope.

Typically, with the exception of the nature and/or the content of coloring agent, the composition of the core and the composition of the envelope are then identical and constitute a single phase.

According to a variant not shown, the capsule 1A is a so-called "simple" capsule, which is understood to mean that the core 3 consists of a single aqueous or oily internal phase that is in contact with the gelled envelope 5. The internal phase may be, for example, one of the internal phases 3A, 3B described above A simple capsule is, for example, described in international applications WO 2010/063937, WO 2011/086331 and WO 2015/071433 in the name of the Applicant.

Envelope

Each external phase 5A, 5B of the gelled envelope 5 of the capsule 1A is a gelled membrane comprising at least one polyelectrolyte in the gelled state chelated by divalent cations to provide the mechanical strength of the capsule 1A.

The gelled envelope 5 may have, for example, a thickness less than 500 µm, advantageously more than 10 µm, typically between 25 µm and 100 µm.

Each of the external phases 5A, 5B may consist, for example, of a hydrogel comprising water and at least one divalent cation-chelated polyelectrolyte, and, optionally, at least one surfactant.

In the context of the present invention, the polyelectrolyte(s) present in the gelled envelope is/are reactive with divalent cations.

For the purposes of the present invention, the term "divalent cation-reactive polyelectrolyte" is understood to mean a polyelectrolyte that is capable of passing from a liquid state in an aqueous solution to a gelled state as a result of contact with a gelling solution containing divalent cations.

The term "divalent cations" is understood to mean, in particular, the cations of the selected alkaline earth metals, for example, from among calcium ($Ca^{2+}$), barium ($Ba^{2+}$) and magnesium ($Mg^{2+}$) cations. Preferably, the divalent cations are calcium ($Ca^{2+}$) cations.

The polyelectrolyte may be, in particular, a natural polysaccharide reagent with multivalent ions such as an alkali alginate, a gellan, a pectin or a carrageenan.

Preferably, the polyelectrolyte is an alginate.

Alginates are advantageously produced from brown algae called "laminaria". Such alginates advantageously have a content of α-L-guluronate mass that is greater than about 50%, preferably greater than 55%, or even greater than 60%.

Preferably, the polyelectrolyte in the gelled state is calcium alginate.

The individual polyelectrolyte chains in the liquid state advantageously have a molar mass greater than 65,000 g/mol.

In the gelled state, the individual polyelectrolyte chains form, with the divalent cations, a coherent three-dimensional network which retains the core 3 and prevents its possible flow. The individual chains are held together and can not flow freely relative to each other. In this state, the viscosity of the formed gel is infinite.

The three-dimensional gel of polyelectrolyte contained in the external phases 5A, 5B traps water (and at least one surfactant when it is present). The weight content of polyelectrolyte in the external phases 5A, 5B may be, for example, between 0.5% and 5% relative to the total weight of the gelled envelope 5.

The surfactant optionally contained in the gelled envelope 5 is advantageously an anionic surfactant, a nonionic surfactant, a cationic surfactant or a mixture thereof. The molecular weight of the surfactant is, for example, between 150 g/mol and 10,000 g/mol, advantageously between 250 g/mol and 1500 g/mol.

In the case where the surfactant is an anionic surfactant, it may be chosen, for example, from alkyl sulphates, alkyl sulphonates, alkyl aryl sulphonates, alkaline alkyl phosphates, dialkyl sulphosuccinates, alkaline earth salts of saturated or unsaturated fatty acids. These surfactants advantageously have at least one hydrophobic hydrocarbon chain having a number of carbons greater than 5 or even 10 and at least one hydrophilic anionic group, such as a sulphate, a sulphonate or a carboxylate linked to one end of the hydrophobic chain.

In the case where the surfactant is a cationic surfactant, it may be chosen, for example, from among alkylpyridium or alkylammonium halide salts such as n-ethyldodecylammonium chloride or bromide, cetylammonium chloride or bromide (CTAB). These surfactants advantageously have at least one hydrophobic hydrocarbon chain having a number of carbon atoms greater than 5 or even 10, and at least one hydrophilic cationic group, such as a quaternary ammonium cation.

In the case where the surfactant is a nonionic surfactant, it may be chosen, for example, from among polyoxyethylenated and/or polyoxypropylenated derivatives of fatty alcohols, fatty acids, or alkylphenols, arylphenols, or from alkylglucosides, polysorbates and cocamides.

According to one embodiment of the invention, the surfactant is sodium lauryl sulphate (SLS or SDS).

The mass content of surfactant in the gelled envelope 5 is greater than 0.001% and is advantageously less than 0.1%.

Second Embodiment of the Capsules

With reference to FIG. 3, a series of capsules according to a second embodiment of the invention is described. The series comprises capsules that are analogous to one another, so that only one capsule 10 of the series will be described.

The capsule 10 is analogous to the capsule 1A shown in FIGS. 1 and 2. The capsule 10 is a "simple" or "complex" capsule in the sense defined above, i.e. it comprises a single-phase or multi-phase core (not shown) as described for the capsule 1A.

Similar elements have the same numerical references and will not be described again. Only the differences will be described in detail below.

The portions 7A, 7B do not have substantially equal areas. For example, the area of the portion 7A is less than $\frac{1}{3}$, preferably less than $\frac{1}{4}$, preferably less than $\frac{1}{6}$, preferably less than $\frac{1}{8}$, preferably less than $\frac{1}{10}$, preferably less than $\frac{1}{12}$, preferably less than $\frac{1}{14}$, preferably less than $\frac{1}{16}$, preferably less than $\frac{1}{18}$, preferably less than $\frac{1}{20}$, and better still less than $\frac{1}{22}$, of the total area of the capsule 10.

The portion 7A forms a narrow sector extending, for example, between two points, or poles, N, S that are diametrically opposed to the external surface 7.

Advantageously, the area of the portion 7A is less than $\frac{1}{10}$, preferably less than $\frac{1}{12}$ of the total area of the capsule 10.

Third Embodiment of the Capsules

With reference to FIGS. 4 and 5, a series of capsules according to a third embodiment of the invention is described. The series comprises capsules that are analogous to one another, so only one capsule of the series will be described.

The capsule 20 is analogous to the capsule 1A shown in FIGS. 1 and 2. Similar elements have the same reference numerals and will not be described again. Only the differences will be described in detail below.

The two external phases 5A, 5B are no longer continuous on the external surface 7 of the capsule 20, and form a plurality of distinct portions 7A, 7B, . . . 7L in the form of sectors ("melon slices") on this external surface.

In this example, the sectors are twelve in number. The sectors formed by the external phase 5A alternate with the sectors formed by the external phase 5B around a polar direction D1 of the capsule 20.

The sectors are advantageously substantially delimited by meridians of the capsule 20, i.e. by substantially circular lines joining two opposite poles N, S of the capsule 20.

Advantageously, the sectors have areas that are substantially equal to each other (e.g. which do not differ, for example, by more than 5% or even more than 2.5% from each other).

According to other variants not shown, the number of sectors is different from twelve. It may be, for example, four, six, eight, ten, or more than twelve.

According to one variant, the sectors have different areas from each other.

According to other variants (not shown), the sectors are formed by more than two external phases, for example three or four or more. The alternation of the external phases around the polar direction D1 is simple (for example 1, 2, 3, 1, 2, 3 . . . , wherein each digit symbolizes a distinct external phase), or, alternatively, follows other more complex patterns (for example 1, 2, 3, 2, 1, 2, 3, 2, 1 . . . ).

According to one variant not shown, the number of sectors may be, for example, odd, and may advantageously be three, five, seven, nine, eleven, or more.

According to yet another variant (not shown), the external phases alternate without forming a regular pattern that is repeated angularly, i.e. in fact the period of the alternation has a number of sectors equal to the total number of sectors (for example a capsule with five sectors 1, 2, 3, 1, 2, 1, 2, 3, 1, 2 . . . ).

Variant of the Third Embodiment of the Capsules

Referring to FIG. 6, a series of capsules according to a variant of the third embodiment of the invention is described. The series comprises capsules that are analogous to one another, so that only one capsule of the series will be described.

The capsule 30 is analogous to the capsule 20 shown in FIGS. 4 and 5. Similar elements have the same reference numerals and will not be described again. Only the differences will be described in detail below.

The sectors formed by the portions 7A, 7B, . . . 7L are no longer delimited by meridians of the capsule 30, but by curved lines 24 (i.e. with a twist) on the external surface 7.

The curved lines 24 extend, for example, substantially between the pole N and the pole S of the capsule 30.

Each of the curved lines 24 may be seen as a meridian deformed on one side and/or on the other on the external surface 7.

According to one variant (not shown), the sectors formed by the sections 7A, 7B are no longer delimited by meridians of the capsule 1A, 10, but by curved lines (i.e. having a twist) on the external surface 7, like the aforementioned curves 24.

Device

Referring to FIG. 7, a device 40 is described that is designed to implement a method according to the invention to produce the capsule 1A and a series of capsules analogous to this capsule.

The device 40 comprises sources 43A, 43B, 45A, 45B respectively supplying the internal phases 3A, 3B and the external phases 5A, 5B in the ungelled state, a nozzle 55 connected upstream of the sources to form a series of liquid bodies 57 by coextrusion, and a gelling bath 59.

The device optionally comprises a system 61 (FIGS. 7 and 9) for supplying a possible gaseous flow 63 to the liquid bodies 57 being formed. It should be noted that the system 61 is not used for the manufacture of the capsules 1A and 10 described above.

The device 40 advantageously also comprises a bath (not shown) for rinsing and storage of the capsules produced.

The nozzle 55 defines a coextrusion axis D2 of the liquid body 57 that is, for example, substantially vertical. The nozzle 55 comprises downstream a tip 65 at the end of which the liquid bodies 57 are formed.

The terms "upstream" and "downstream" are understood to mean with respect to the direction of flow of the internal phases 3A, 3B and the external phases 5A, 5B in the nozzle 55.

The nozzle 55 delimits an internal duct 67 extending, for example, along the axis D2 to convey the internal phase 3A, and an external duct 69 coaxial with the internal duct to convey the internal phase 3B and the external phases 5A, 5B. The nozzle 55 also defines a system 71 for supplying the internal phase 3B to the external conduit 69, and a delivery system 73 for the external phases 5A, 5B to the external duct.

The internal duct 67 is separated from the external duct 69 by a first envelope 75, for example of tubular form. The internal duct 67 is connected upstream to the source 43A and opens downstream at the tip 65 of the nozzle.

The external duct 69 is delimited radially internally by the first envelope 75, and radially externally by an external envelope 77, preferably tapering downstream, and preferably extending into a tube 79, for example of metal.

The external duct 69 is connected upstream to the systems 71, 73 and opens downstream at the tip 65 of the nozzle.

The system 71 comprises a supply channel 81 connected to the source 43B, a collector 83, an annular duct 85 coaxial with the internal duct 67 and opening into the external duct 69, and a connecting duct 87 connecting the collector 83 to the annular duct 85 and advantageously creating a pressure drop.

The term "collector" is understood to mean a reservoir having a sufficient volume so that the flow of the relevant phase in the reservoir is slow and allows homogenization of the pressure of the phase in the reservoir. Thus, the flow from this reservoir is conditioned by the structure of the nozzle 55 downstream of the reservoir and not by the manner in which the reservoir is fed.

Thus, thanks to the pressure drop created by the connecting duct 87, it is possible to regulate the flow rate downstream of the pressure drop and to homogenize the flow injected into the annular duct 85 and thus into the external duct 69.

The annular duct 85 is advantageously delimited internally by the first envelope 75.

The collector 83 is advantageously symmetrical about the axis D2, and may be toric, for example.

The connecting duct 87 is, for example, symmetrical about the axis D2. The connecting duct 87 extends from the top of the collector 83 to a bend 89 located higher than the collector 83 in order to allow evacuation of any bubbles present in the flow.

The system 73 is advantageously similar to the system 71, except that, in this example, it comprises two supply channels 91, 93 respectively connected to the sources 45A, 45B. The system 73 also comprises a collector 95, an annular duct 97, and a connecting duct 99.

The annular duct 97 opens into the external duct 69. The annular duct 97 is radially further away from the axis D2 than the annular duct 85, and is separated from the latter by an intermediate envelope 101 which does not extend to the tip 65 of the nozzle.

The supply channels 91, 93 may open, for example, into diametrically opposite areas of the collector 95.

The gelling bath 59 may be located, for example, directly above the nozzle 55.

The gelling bath 59 comprises a gelling solution 100 comprising at least one reagent, for example $Ca^{2+}$ cations, that is capable of reacting with the polyelectrolyte(s) of each of the external phases 5A, 5B of the liquid body 57 in order to pass the polyelectrolyte(s) from a liquid state to a gelled state.

Method

A method according to the invention, implemented in the device 40, will now be described with reference to FIG. 7. The method makes it possible to manufacture the capsule 1A and a series of analogous capsules.

The method comprises a step of conveying a first flow F1 of the internal phases 3A, 3B, and a second flow F2 of the two external phases 5A, 5B in the ungelled state, and a step of successive formation of liquid bodies 57 starting from the first flow and the second flow.

The method advantageously comprises a step of letting fall the liquid bodies 57 through a volume of air 103, and a step of immersing each liquid body in the gelling bath 59 to obtain the capsules.

The method comprises an optional step of rinsing/storing the capsules.

The source 43A supplies the internal duct 67 with an internal phase flow 3A.

The source 43B supplies the collector 83 in the internal phase 3B via the supply channel 81. The internal phase 3B then flows into the annular duct 85.

The internal phase flow 3A in the internal duct 67, and the internal phase flow 3B in the annular duct 85 and in the external duct 69 together form the first flow F1. In this example, the first flow F1 comprises two flows that are physically separated by the first envelope 75.

The collector 95 surrounds the first flow F1 around a local circulation direction D3 of the first flow.

The local circulation direction D3 is, in this example, coincident with the axis D2 of the nozzle 55.

The sources 45A and 45B supply the external phase collector 95 5A, 5B in the ungelled state via the supply channels 91, 93. This creates two distinct supply areas 105A, 105B in the collector 95, which alternate angularly around the local circulation direction D3.

Then, the external phases 5A, 5B are discharged from the supply areas 105A, 105B homogeneously into the annular duct 97, in which they form the second flow F2.

The second flow F2 surrounds the first flow F1. The second flow F2 is annular in the annular duct 97, then always converges annularly in the external duct 69, and remains annular at the tip 65.

In the external duct 69, the second flow F2 is not physically separated from the first flow F1, but does not mix appreciably with the first flow taking into account the movement speeds of the flows F1 and F2 that are greater than the speed of possible mixing of the flows F1 and F2. Similarly, the second flow F2 comprises a flow of each external phase 5A, 5B that do not mix appreciably with each other taking into account the movement speeds of each external phase 5A, 5B that are greater than the possible mixing speed of the external phase flows 5A, 5B.

At the outlet of the nozzle 55, the internal phase 3A comes into contact with the internal phase 3B, while the two external phases 5A, 5B come into contact with the first flow F1 formed by the internal phases 3A, 3B.

In the tip 65, each of the two external phases 5A, 5B is in contact with the tube 79.

The liquid bodies 57 are substantially spherical. Each liquid body 57 comprises a drop 107 formed by the internal phases 3A and 3B, and a peripheral film 109 coating the drop and with the two external phases 5A, 5B well separated.

The optional system 61 is not used for the manufacture of the capsule 1A.

The film 109 has on its external surface two distinct portions 109A, 109B that are respectively formed by the two external phases 5A, 5B in the ungelled state.

The liquid bodies 57 detach from the nozzle 55 advantageously under the effect of gravity, and fall through the volume of air 103. The method is therefore carried out through dripping.

However, the method according to the invention may also operate continuously by separation jetting. According to this embodiment, the method then comprises:
- a step of forming at the nozzle outlet 55 a jet formed by the flow F2 concentrically surrounding the flow F1, then
- a step of forming a plurality of liquid bodies 57 by fragmenting the jet in the volume of air 103 under the effect of gravity.

When the liquid bodies 57 arrive in the solution 100, the external phases 5A, 5B pass to the gelled state, while the liquid bodies 57 become capsules such as the capsules 1A, 1B, 1C.

The flow rates and viscosities of the different phases required for the manufacture of capsules according to the invention are within the general skills of those skilled in the art.

The injection rates in external phases 5A and 5B in the nozzle 55 may be identical or different. With identical flow rates, capsules are obtained in which the portion 7A has an area substantially equal to that of the portion 7B, as in the capsule 1A.

With different flow rates, different areas are obtained.

If the ratio of the external phase flow rate 5A divided by the total flow rate of the second flow F2 is lower than, for example, $\frac{1}{3}$, $\frac{1}{4}$, $\frac{1}{6}$, $\frac{1}{8}$, $\frac{1}{10}$, $\frac{1}{12}$, $\frac{1}{14}$, $\frac{1}{16}$, $\frac{1}{18}$, $\frac{1}{20}$, and preferably less than $\frac{1}{22}$, a capsule like the capsule 10 shown in FIG. 3 is obtained.

According to a particular embodiment, the liquid solutions each comprising at least one clean liquid polyelectrolyte to be gelled may also differ from each other in order to ensure the formation of a gelled envelope 5 which may have mechanical heterogeneity. This may, in particular, contribute to creating break points of the gelled envelope. This mechanical heterogeneity may result, in particular in:
- the choice of polyelectrolytes, in particular the ratio G (guluronate)/M (mannuronate) when the polyelectrolyte is alginate, and/or
- the respective concentrations of polyelectrolytes in the external phases 5A, 5B in the ungelled state.

Variant of the Device

Referring to FIG. 8, a device 140 constituting a variant of the device 40 is described. The device 140 is analogous to the device 40 shown in FIG. 7. The similar elements have the same reference numerals and will not be described again. Only the differences will be described in detail below.

The device 140 differs in that it comprises a plurality of supply channels 191 (six in the example) connected to the source 45A, and a plurality of supply channels 193 (six in the example) connected to the source 45B. The channels may be distinct or result from the branching of a common trunk.

The supply channels 191, 193 form inlet orifices 195 in the collector 95 which are angularly successive around the local circulation direction D3.

This creates a plurality of distinct supply areas 191A, 193A in the collector 95, which angularly alternate around the local circulation direction D3.

It is thus possible to manufacture capsules such as the capsule 20 shown in FIGS. 4 and 5.

Variant of the Method

Referring to FIG. 9, in a variant, the method comprises an optional step of applying a gaseous flow 63, in particular a flow of air, to each of the liquid bodies 57 being formed.

The gaseous flow 63 has a tangential component T with respect to the axis D2, which rotates the liquid bodies 57 being formed and allows, for example, the obtaining of liquid bodies comprising sectors 222 prefiguring the sectors 7A, 7B, . . . 7L of the capsule 30 shown in FIG. 6.

Depending on the desired aesthetic effect, it is possible to operate on the pressure and/or the flow rate of the gaseous flow and/or the ejection diameter of the system 61 in order to modify the speed of rotation of the liquid body 57 and so obtain a more or less pronounced spiral visual effect.

We may also:
adapt the average angle of the air flow 63 made with the axis D2 of the nozzle 55, preferably between 45° and 135°, and/or
adapt the distance D between the output of the system 61 and the liquid body 57 being formed, preferably between 2 mm and 15 mm.

The area of contact between the gaseous flow 63 and the liquid body 57 being formed may be at:
(i) an upper area,
(ii) a central area, and/or
(iii) a lower area,
of the liquid body 57 being formed with respect to the axis D2.

The contact area is preferably located at the central area.

The gaseous flow 63 may comprise at least one coloring agent, in particular chosen from the group comprising pigments, nacres (flakes), optically effective materials, in particular liquid crystals, and mixtures thereof, preferably pigments and/or nacres.

Alternatively (not shown), several air flows may be applied to the liquid bodies 57, in particular with:
different orientations, if necessary positioned at different heights along the axis D2 to produce turns which change their trajectory in the polar direction D1 of the capsules, and/or
wherein at least one air flow, or even each air flow, also comprises at least one coloring agent, wherein the colors are different or at least in different amounts.

In addition, it is possible to modify the moisture saturation of the gaseous flow 63 to prevent drying of the film 109, in particular on the tip of the nozzle 55 (i.e. at the tip 65 of the nozzle).

The air supply pressure at the outlet of the system 61 is advantageously adjusted to obtain a speed of the air flow 63 at the liquid body 57 being formed, that is sufficient to obtain the expected rotation effect, and below an upper limit at which undesired tearing of the liquid body 57 being formed may occur. In particular, this relative pressure is less than 1 bar, preferably less than 0.5 bar.

In particular, this relative pressure is between 50 millibars and 900 millibars, preferably between 100 millibars and 700 millibars, and better between 200 millibars and 400 millibars.

Advantageously, when the method according to the invention comprises the application of the gaseous flow 63, the flow rates of the different phases are reduced in the nozzle 55. Thus, the liquid body 57 being formed has a longer time to turn, which has an impact on the intensity of the spiral pattern so formed. Preferably, the flow rates of the different phases are reduced by about 50% compared with the same flow rates in a method without application of a gaseous flow 63.

Other Variants of the Device

Referring to FIG. 10, a device 340 constituting a variant of the device 40 is described. The device 340 is analogous to the device 40 shown in FIG. 7. The similar elements have the same reference numerals and will not be described again. Only the differences will be described in detail below.

The nozzle 55 of the device 340 does not have a first envelope 75 which physically separates the internal phases 3A and 3B up to the outlet of the nozzle. On the other hand, the nozzle 55 comprises an intermediate envelope 301 that physically separates the second flow F2 from the first flow F1 to the outlet.

Referring to FIG. 11, a device 440 constituting another variant of the device 40 is described. The device 440 is similar to the device 40. The analogous elements have the same reference numerals and will not be described again. Only the differences will be described in detail below.

The nozzle 55 of the device 440 comprises an intermediate envelope 401 that physically separates the second flow F2 from the first flow F1 to the outlet. Thus, the nozzle 55 comprises three envelopes separating the internal phase 3A, the internal phase 3B, and the second flow F2.

According to a variant shown in FIG. 12, the system 61 comprises two subsystems 61A, 61B for respectively applying two gaseous flows 63A, 63B to the liquid bodies 57 being formed.

Each of the subsystems 61A, 61B comprises, for example, a nozzle, wherein the nozzles are arranged so that the gaseous flows 63A, 63B are opposite to each other and substantially tangential to the surface of the liquid bodies 57 being formed.

The points of impact of the gaseous flows 63A, 63B on the liquid bodies 57 are, for example, diametrically opposite to one another.

This makes it possible to improve the detachment of the liquid bodies 57 from the nozzle 55 and makes it possible to obtain a greater spiral effect on a capsule, such as the capsule 30 shown in FIG. 6.

Cosmetic Composition and Cosmetic Treatment Method

According to one embodiment, the composition of the invention is a cosmetic composition in combination with a physiologically acceptable medium or a cosmetically-acceptable receiving medium. The term "physiologically acceptable medium" or "a cosmetically-acceptable receiving medium" is understood to mean a medium that is particularly suitable for the application of a composition according to the invention to keratinous materials, in particular the skin, the lips, the nails, eyelashes or eyebrows, and preferably the skin.

The physiologically acceptable medium is generally adapted to the nature of the support to which the composition is to be applied, as well as to the appearance under which the composition is to be packaged. In particular, the medium has a viscosity that is sufficient to ensure suspension of the capsules and thus avoid any phenomenon of sedimentation or creaming of the capsules in the medium. In fact, for obvious reasons, the suspending nature of the medium may participate in reinforcing the attractive and novel visual capsules according to the invention.

The present invention also relates to a non-therapeutic cosmetic treatment method of the skin comprising a step of applying to the skin at least one layer of the composition according to the invention.

This method is preferably carried out with a composition comprising capsules whose active ingredient(s) is/are non-therapeutic cosmetic active ingredients.

It may be, in particular, a cosmetic composition.

Another object of the invention is the cosmetic use of the cosmetic composition described above.

The receiving medium of the capsules may be, for example, an aqueous composition.

The aqueous composition may be liquid or gelled.

When gelled, the aqueous composition is in the form of an "aqueous gel", i.e. it is a solution comprising water and a gelling agent.

In the context of the present description, the term "gelling agent" means a compound capable of giving a composition the consistency of a gel.

The gelling agent is preferably selected from the group consisting of polysaccharides, galactomannans, polysaccharides, glycosaminoglycans, polyols and mixtures thereof.

Advantageously, it may be chosen from the group consisting of xanthan gum, carrageenan, carob, guar gum, gellan, hyaluronic acid, glycerol, propanediol, cellulose or its derivatives, and their mixtures.

Preferably, the aqueous composition has a viscosity of less than 50 Pa·s as measured at 25° C., preferably less than 20 Pa·s. Advantageously, the aqueous composition (A) may have a viscosity of 2 Pa·s at 15 Pa·s as measured at 25° C.

Such a viscosity of the aqueous gel allows good suspension of the capsules, in particular over a period of at least one month, at a temperature of 40° C.

According to one variant, the composition does not suspend the capsules, i.e. they settle in the composition (A). For this purpose, it is, in particular, possible to use a composition (A) with a viscosity of less than 2 Pa·s.

Advantageously, the aqueous gel is transparent so that the consumer may visualize the capsule. Its texture may be chosen according to the texture that is desired for the composition according to the invention.

The viscosity is measured by the following method, in particular as described in the international application WO 2013/132082 in the name of the Applicant.

Preferably, the weight percentage of water of the aqueous gel is at least 70%, especially 70% to 85%, preferably 70% to 80%, based on the total weight of the composition.

The aqueous composition may also comprise a cosmetic, dermopharmaceutical, pharmaceutical, fragrance or food agent as defined above.

The aqueous composition may also comprise a preservative, a coloring agent, in particular pigments, and/or nacres.

Typically, the mass ratio between the aqueous composition and the capsules is from 30/70 to 70/30, preferably from 40/60 to 60/40.

Advantages

With the characteristics described above, the invention provides compositions having a novel visual appearance, derived from the implementation of capsules with a particular structure, preferably monodisperse, inexpensive to manufacture and designed to preserve the integrity of the encapsulated ingredients (i.e. reduce, or even prevent, their subsequent aging, in particular, oxidation, enzymatic and/or ionic degradation, etc.) while being designed for multiple uses, especially in the cosmetic field, even the pharmaceutical or agri-food industry.

As the gelled envelope 5 comprises at the surface 7 at least two distinct portions 7A, 7B respectively formed by the two external phases 5A, 5B, at least one of which comprises at least one coloring agent, the invention has the technical effect of the capsules having at least two areas that are perceived as distinct by a user, more directly than with the capsules of the prior art.

In some embodiments, the existence of these areas confers on the capsules new chemical properties, by incorporating specific products into one or more of the distinct phases of the gelled envelope 5.

The invention thus provides an ingredient encapsulation system with an unprecedented visual appearance and ensures a controlled release/diffusion of encapsulated ingredients.

In addition, thanks to the invention, it is possible to create at least one area of weakness of the capsules. For example, one of the phases of the gelled envelope 5 may advantageously comprise a level of gelled polyelectrolyte, in particular of alginate, lower than that of the other phases of the envelope, which makes it locally less mechanically resistant. This phase may advantageously form a streak on the surface of the gelled envelope 5 and thus constitute a line of weakness of the capsule.

The invention also provides a competitive method for achieving these results.

Throughout the present description, including the claims, the phrase "comprising one" should be understood as being synonymous with "comprising at least one", unless the contrary is specified.

The expressions "comprised between . . . and . . . ", "comprised from . . . to . . . " and "from . . . to . . . " must be understood as being inclusive, unless otherwise specified.

The amounts of the ingredients in the examples are expressed as percentage by weight relative to the total weight of the composition, unless otherwise indicated.

The examples which follow illustrate the present invention without limiting its scope.

EXAMPLES

Experimental Apparatus

In the two examples below, the method for preparing capsules, such as capsule 1A, is based on the concentric coextrusion of compositions (or phases) via a triple-envelope millifluidic device, such as the device 440 shown in FIG. 11, to form multi-component drops such as liquid bodies 57.

The compositions of the internal phases 3A and 3B, and external phases 5A and 5B for the manufacture of capsules are described in the table below in % by weight.

| Phase | Commercial designation | Supplier | INCI | % | %/capsule |
|---|---|---|---|---|---|
| Internal phase 3A | Refined vegetable oil of apricot kernel | Ardex | *PRUNUS ARMENIACA* KERNEL OIL | 100.00 | 16.67 |
| | | | Total | 100.00 | 16.67 |
| Internal phase 3B | Reverse osmosis water | — | AQUA | qsf | qsf |
| | Microcare PE | Thor | PHENOXYETHANOL, AQUA | 0.80 | 0.53 |
| | Microcare emollient PTG | Thor | PENTYLENE GLYCOL, AQUA | 2.00 | 1.33 |
| | Protanal LF 200 FTS | FMC Bio polymer | ALGIN | 0.03 | 0.02 |
| | Phylcare sodium hyaluronate CPS | Biophil | SODIUM HYALURONATE | 0.95 | 0.63 |
| | | | Total | 100.00 | 66.67 |
| External phase 5A | Reverse osmosis water | — | AQUA | 92.06 | 14.11 |
| | Microcare PE | Thor | PHENOXYETHANOL. AQUA | 0.80 | 0.12 |
| | Microcare emollient PTG | Thor | PENTYLENE GLYCOL. AQUA | 2.00 | 0.31 |
| | Protanal LF 200 FTS | FMC Bio polymer | ALGIN | 2.00 | 0.31 |
| | Sodium Dodecyl sulfate PRS Codex | Panreac | SODIUM LAURYL SULFATE | 0.14 | 0.02 |
| | Sunshine Soft White | Sunchemical | SYNTHETIC FLUORPHLOGOPITE (AND) TITANIUM DIOXIDE | 3.00 | 0.46 |
| | | | | 100.00 | 15.33 |
| External phase 5B | Reverse osmosis water | — | AQUA | 92.06 | 1.23 |
| | Microcare PE | Thor | PHENOXYETHANOL. AQUA | 0.80 | 0.01 |
| | Microcare emollient PTG | Thor | PENTYLENE GLYCOL. AQUA | 2.00 | 0.03 |
| | Protanal LF 200 FTS | FMC Bio polymer | ALGIN | 2.00 | 0.03 |
| | Sodium Dodecyl sulfate PRS Codex | Panreac | SODIUM LAURYL SULFATE | 0.14 | 0.002 |
| | Colorona mica black | Merck | | 3.00 | 0.04 |
| | | | Total | 100.00 | 1.33 |

Formation of Gelled Capsules

At the outlet of the triple envelope, a multi-component drop then forms, wherein the first flow F1, formed by the internal phases 3A, 3B, constitutes the core, while the second flow F2 constitutes the external liquid envelope of the multi-component drop. The core is more particularly constituted by an internal drop formed by the internal phase 3A, in an intermediate envelope formed by the internal phase 3B.

The size of the internal drop, the thickness of the intermediate envelope and the external envelope of the capsules so formed are controlled by the use of several independent syringe pumps to regulate the injection rates of the various compositions forming the internal phases 3A, 3B and the external phases 5A, 5B.

Each multi-component drop is detached from the triple envelope and falls into a volume of air, before being immersed in a gelling solution of concentrated calcium at 1M.

Once the external shell has gelled, the gelled capsules thus formed are rinsed in a water-based rinse solution.

Example 1

The millifluidic device used is a coaxial three-way nozzle, with a collector 95 as represented in FIG. 8.

The flow rates of the different phases are as follows:
internal phase 3A: 10 ml/h,
internal phase 3B: 40 ml/h,
external phase 5A: 9.2 ml/h, and
external phase 5B: 0.8 ml/h.

The method according to the invention makes it possible to obtain capsules of uniform size presenting a novel visual appearance. In fact, each capsule comprises twelve portions 7A to 7L forming sectors, wherein sectors of the same color are opposed in pairs, while the white sectors are much wider than the black sectors (substantially in the ratio of the flow rates of the external phases 5A and 5B).

Example 2

With Application of an Air Flow

The millifluidic device used is a coaxial three-way nozzle in which the collector 95 is supplied with external phases 5A, 5B only by two main channels, as in the device 40 shown in FIG. 7.

The flow rates of the different phases are as follows:
internal phase 3A: 5 ml/h,
internal phase 3B: 20 ml/h,
external phase 5A: 4.6 ml/h, and
external phase 5B: 0.4 ml/h.

The method implemented further comprises the direction of the air flow 63 towards the contact area between the drop forming at the outlet of the triple jacket, wherein the direction is tangential to one side of the drop in formation at the device output 40.

The air flow 63 has the following characteristics:
air pressure: 200 mbar
internal diameter of the air supply tube: 0.9 mm,
angle with respect to the vertical axis D2: 90°,
distance between the outlet of the air supply tube and the film 109 of the drop being formed: 8 mm.

The air flow 63 causes rotation of the drop being formed at the outlet of the millifluidic device relative to the vertical axis D2 of the device (perpendicular to the direction of expansion of the drop).

The method according to the invention makes it possible to obtain capsules of uniform size and endowed with a novel visual appearance. In fact, each capsule comprises two portions 7A, 7B, wherein the white portion 7A is very wide, while the black portion 7B is very narrow (as in the case of the capsule 10 shown in FIG. 3) and forming a spiral pattern over the entire envelope of the gelled capsules (as in the case of the capsule 30 shown in FIG. 6).

The invention claimed is:

1. A method for producing a series of capsules, wherein each capsule of the series of capsules comprises a core which is liquid or at least partially gelled or at least partially thixotropic, and a gelled envelope completely encapsulating the core and comprising at least two external phases, wherein each of said at least two external phase contains at least one gelled polyelectrolyte, and wherein the gelled envelope has an external surface having at least two distinct portions respectively formed by said at least two external phases, wherein the method comprises the steps of:

conveying a first flow of one or more internal phase(s) that are intended to form the core, and a second flow of said at least two external phases that are intended to form the gelled envelope, wherein each of said at least two external phases contains at least one liquid polyelectrolyte capable of gelling, at least one of said at least two external phases comprising at least one coloring agent, and wherein the second flow surrounds the first flow about an axis;

successive formation, from the first flow and the second flow, of a plurality of liquid bodies, wherein each liquid body of the plurality of liquid bodies comprises a drop of said one or more internal phase(s), and a peripheral film coating the drop and having said at least two external phases, and wherein the film has on its external surface said at least two distinct portions formed respectively by said at least two external phases; and immersing each liquid body of the plurality of liquid bodies in a gelling solution containing a reagent adapted to react with said at least one liquid polyelectrolyte of each of said at least two external phases to form one capsule of the series of capsules, and recovering the series of capsules.

2. The method according to claim 1, further comprising applying a gaseous flow to each liquid body of the plurality of liquid bodies being formed in order to deform said at least two distinct portions of the external surface of the film by rotation about the axis, wherein the gaseous flow has a tangential component with respect to the axis.

3. The method according to claim 1, wherein during the step of forming the plurality of liquid bodies, said at least two external phases are in contact with the first flow.

4. The method according to claim 1, wherein:
the conveying is carried out in at least one nozzle defining the axis, wherein each of said at least two external phases is in contact with an external envelope of said at least one nozzle at an outlet of said at least one nozzle, and
the plurality of liquid bodies is formed at an outlet of said at least one nozzle, wherein the method comprises a step of detaching the plurality of liquid bodies from said at least one nozzle.

5. The method according to claim 4, wherein the conveying step comprises:
letting out the second flow from at least one collector formed by said at least one nozzle, wherein the collector surrounds the first flow about a local circulation direction of the first flow, and
feeding said at least one collector from at least two sources supplying said at least two external phases to create a plurality of distinct supply areas in said at least one collector, wherein each of the plurality of distinct supply areas is filled by one or the other of said at least two external phases, some of the plurality of supply areas filled by one of said at least two external phases alternating with others of the plurality of supply areas filled by the other of said at least two external phases around the local circulation direction.

6. The method according to claim 5, wherein said at least one nozzle forms a plurality of supply channels of said at least one collector, and wherein the plurality of supply channels is connected to said at least two sources to form inlet ports in said at least one collector, wherein the inlet ports are angularly successive about the local circulation direction.

7. The method according to claim 5, wherein one of the plurality of supply areas is supplied at a first flow rate in one or other of said at least two external phases, and another one of the plurality of supply areas is supplied at a second flow rate in one or other of said two external phases, wherein the first flow rate is lower than the second flow rate.

8. The method according to claim 7, wherein the ratio of the first flow rate divided by the second flow rate is less than ⅓.

9. The method according to claim 4, wherein the conveying step comprises a physical separation of the first flow and the second flow at the outlet of said at least one nozzle by an envelope of said at least one nozzle.

10. A series of capsules manufactured by a method according to claim 1, wherein each capsule of the series of capsules comprises:
a core which is liquid or at least partially gelled or at least partly thixotropic, wherein the core comprises one or more internal phases, and
a gelled envelope completely encapsulating the core and comprising at least two external phases, wherein each of said at least two external phases contains a gelled polyelectrolyte, wherein at least one of said at least two external phases comprises a coloring agent, and wherein the gelled envelope has an external surface with at least two distinct portions respectively formed by said at least two external phases.

11. The series of capsules according to claim 10, wherein, for each capsule of the series of capsules, the external surface of the gelled envelope comprises a plurality of portions formed by said at least two external phases, and wherein the plurality of portions forms sectors alternating about a polar direction of said each capsule.

12. The series of capsules according to claim 11, wherein the sectors extend substantially between a pole of each capsule of the series of capsules and an opposite pole according to the polar direction, and wherein the sectors are approximately delimited:
either by meridians of said each capsule,
or by curved lines extending substantially between the pole and the opposite pole.

13. The series of capsules according to claim 10, wherein said at least two external phases of the gelled envelope are in contact with the core.

14. A composition comprising a series of capsules according to claim 10, and a medium for receiving the series of capsules.

15. A non-therapeutic method for cosmetic treatment of a keratinous material, comprising at least one step of applying to the keratinous material at least one composition according to claim 14.

16. The method according to claim 8, wherein the ratio of the first flow rate divided by the second flow rate is less than $1/4$.

17. The method according to claim 8, wherein the ratio of the first flow rate divided by the second flow rate is less than $1/6$.

18. The method according to claim 8, wherein the ratio of the first flow rate divided by the second flow rate is less than $1/8$.

19. The method according to claim 8, wherein the ratio of the first flow rate divided by the second flow rate is less than $1/10$.

20. The composition according to claim 14, wherein the composition is a cosmetic composition.

\* \* \* \* \*